(12) United States Patent
Hsieh et al.

(10) Patent No.: US 10,555,888 B2
(45) Date of Patent: Feb. 11, 2020

(54) NAIL COMPOSITIONS CONTAINING LATEX AND SULFOPOLYESTER COMPOUND

(71) Applicant: L'ORÉAL, Paris (FR)

(72) Inventors: I-Fan Hsieh, Scotch Plains, NJ (US); Christopher Michael MacNeill, Fanwood, NJ (US); XianZhi Zhou, Millburn, NJ (US); Ramakrishnan Hariharan, Springfield, NJ (US)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 15/832,033

(22) Filed: Dec. 5, 2017

(65) Prior Publication Data

US 2019/0167556 A1 Jun. 6, 2019

(51) Int. Cl.
*A61K 8/81* (2006.01)
*A61K 8/85* (2006.01)
*A61Q 3/02* (2006.01)

(52) U.S. Cl.
CPC .......... *A61K 8/8117* (2013.01); *A61K 8/8147* (2013.01); *A61K 8/8152* (2013.01); *A61K 8/85* (2013.01); *A61Q 3/02* (2013.01); *A61K 2800/30* (2013.01)

(58) Field of Classification Search
CPC ............ A61K 2800/30; A61K 8/8117; A61K 8/8147; A61K 8/8152; A61K 8/85; A61Q 3/02
See application file for complete search history.

(56) References Cited

U.S. PATENT DOCUMENTS

| | | | | |
|---|---|---|---|---|
| 5,082,734 A | * | 1/1992 | Vaughn | .................. C23C 18/30 252/500 |
| 5,204,401 A | * | 4/1993 | Anderson, Jr. | ...... C08G 18/283 524/441 |
| 5,266,322 A | | 11/1993 | Myers et al. | |
| 6,844,390 B2 | * | 1/2005 | Kuo | ....................... C08F 265/02 428/480 |
| 8,790,669 B2 | | 7/2014 | Li et al. | |
| 8,889,108 B2 | | 11/2014 | Li et al. | |
| 9,022,546 B1 | * | 5/2015 | Breton | ................ B41M 5/0256 347/102 |
| 2013/0118517 A1 | * | 5/2013 | Foley | ..................... A61K 8/042 132/200 |
| 2014/0328780 A1 | | 11/2014 | Li et al. | |
| 2015/0098971 A1 | | 4/2015 | Sacripante et al. | |
| 2015/0119510 A1 | * | 4/2015 | Eliyahu | .................. C09D 11/30 524/167 |
| 2015/0342863 A1 | | 12/2015 | Li et al. | |
| 2016/0262993 A1 | * | 9/2016 | Ilekti | ........................ A61K 8/39 |
| 2017/0014329 A1 | | 1/2017 | Yakubov et al. | |

FOREIGN PATENT DOCUMENTS

| | | |
|---|---|---|
| WO | WO 2013/048919 A1 | 4/2013 |
| WO | WO 2014/088568 A1 | 6/2014 |
| WO | WO 2014/130437 A1 | 8/2014 |

OTHER PUBLICATIONS

International Search Report and Written Opinion dated Feb. 26, 2019 in PCT/US2018/062447, 16 pages.

* cited by examiner

*Primary Examiner* — Mark V Stevens
(74) *Attorney, Agent, or Firm* — Oblon, McClelland, Maier & Neustadt, L.L.P.

(57) ABSTRACT

The invention relates to nail compositions including water, at least one high molecular weight latex comprising at least one styrene group, at least one latex lacking styrene groups, and at least one low molecular weight sulfopolyester compound, as well as to methods relating to application of such nail compositions.

23 Claims, No Drawings

NAIL COMPOSITIONS CONTAINING LATEX AND SULFOPOLYESTER COMPOUND

FIELD OF THE INVENTION

The present invention relates to nail compositions comprising water, at least one high molecular weight latex comprising at least one styrene group, at least one latex lacking styrene groups, and at least one low molecular weight sulfopolyester compound.

DISCUSSION OF THE BACKGROUND

In recent years, consumers have become more aware of the ingredients contained in their cosmetic formulations and there has been a push for more natural materials or raw materials sourced from natural origins. Nail enamel compositions have lagged behind this trend primarily due to the difficulties with finding an alternative to nitrocellulose. Also, nail enamels typically contain harsh solvents such as butyl acetate, ethyl acetate and alcohols, which affects perception of the products.

Recently, water-based nail enamels have emerged as an alternative to nail enamels that contain harsh chemicals. The primary film former found in water-based nail enamels is typically a polymer or copolymer dispersed in water (latex or latex blend). Nail compositions containing latex are disclosed, for example, in U.S. 2017/0014329, U.S. 2014/0328780, U.S. Pat. Nos. 8,790,669, and 8,889,108. However, these nail compositions are not ideal and they tend to underperform in terms of their wear properties and their removability can be very difficult compared to their nitrocellulose-based counterparts.

There remains a need for nail compositions which are safe and adhere well to nails, yet which can be easily removed with less damage to nails and with more time efficiency.

SUMMARY OF THE INVENTION

The present invention relates to a nail composition comprising water, at least one high molecular weight latex comprising at least one styrene group, at least one latex lacking styrene groups, and at least one low molecular weight sulfopolyester compound. Preferably, the nail composition is free of wax and/or contains less than 5% coloring agent.

The present invention also relates to a nail composition set comprising (1) at least one color coat comprising at least water, one coloring agent, at least one high molecular weight latex comprising at least one styrene group, at least one latex lacking styrene groups, and at least one low molecular weight sulfopolyester compound, and (2) at least one additional coat selected from the group consisting of a topcoat, a basecoat, and a primer. Preferably, the color coat is free of wax and/or contains less than 5% coloring agent.

The present invention further relates to methods for making up and/or protecting nails comprising applying to the nails at least one nail composition comprising water, at least one high molecular weight latex comprising at least one styrene group, at least one latex lacking styrene groups and at least one low molecular weight sulfopolyester compound. Preferably, the nail composition is free of wax and/or contains less than 5% coloring agent. Also preferably, at least one additional composition selected from the group consisting of a topcoat, a basecoat and a primer is applied to the nail or nail composition.

The present invention also relates to a kit comprising (1) a nail composition comprising water, at least one high molecular weight latex comprising at least one styrene group, at least one latex lacking styrene groups, and at least one low molecular weight sulfopolyester compound, and (2) at least one additional composition selected from the group consisting of a topcoat, a basecoat and a primer. Preferably, the nail composition is free of wax and/or contains less than 5% coloring agent.

The present invention also relates to methods for improving removal properties of a nail composition comprising water, at least one high molecular weight latex comprising at least one styrene group and at least one latex lacking styrene groups comprising adding at least one low molecular weight sulfopolyester compound during preparation of the nail composition in an amount sufficient to improve removal properties of the nail composition. Preferably, the nail composition is free of wax and/or contains less than 5% coloring agent.

The present invention further relates to methods for improving adhesion properties of a nail composition comprising water, at least one high molecular weight latex comprising at least one styrene group and at least one latex lacking styrene groups comprising adding at least one low molecular weight sulfopolyester compound during preparation of the nail composition in an amount sufficient to improve adhesion properties of the nail composition. Preferably, the nail composition is free of wax and/or contains less than 5% coloring agent.

The present invention further relates to methods for improving both adhesion properties and removal properties of a nail composition comprising water, at least one high molecular weight latex comprising at least one styrene group and at least one latex lacking styrene groups comprising adding at least one low molecular weight sulfopolyester compound during preparation of the nail composition in an amount sufficient to improve adhesion and removal properties of the nail composition. Preferably, the nail composition is free of wax and/or contains less than 5% coloring agent.

It is to be understood that both the foregoing general description and the following detailed description are exemplary and explanatory only, and are not restrictive of the invention.

DETAILED DESCRIPTION OF THE INVENTION

As used herein, the expression "a" and "at least one" mean one or more and thus includes individual components as well as mixtures/combinations.

Other than in the operating examples, or where otherwise indicated, all numbers expressing quantities of ingredients and/or reaction conditions are to be understood as being modified in all instances by the term "about," meaning within 10% to 15% of the indicated number.

"Film-former" or "film-forming agent," as used herein means a polymer or resin that leaves a film on the substrate to which it is applied, for example, after a solvent accompanying the film former has evaporated, absorbed into and/or dissipated on the substrate.

"Adhesion," as used herein, refers to chemical or physical bonding between a coating and a substrate. Good adhesion between nail polish and nail surface should translate to good wear properties on consumers. Adhesion properties can be quantified by in-vitro method such as a cross-cut adhesion test. In the test, a lattice pattern is cut into the coating and penetrates through to the substrate. A pressure sensitive tape is applied to the sample and then pulled off. The adhesion property can be quantified by the area of the coating remaining after peeling. For example, if the whole film remains after peeling, it indicates excellent adhesion. If most of the film gets peeled off, it indicates poor adhesion. The cross-cut test is an industrial standard test for testing adhesion for coatings. (Reference #ISO/DIN 2409, ASTM D3359).

"Removal properties," as used herein, refers to removing nail compositions or nail composition sets from nails. "Easy removal properties" for a removal process refer to processes which are not time-consuming and/or which do not substantially damage nails. Removal properties can be evaluated, for example, by comparing removability of a composition using a removal solvent (for example, acetone, alcohol or ethyl acetate) with removability of other compositions (including commercially-available compositions) using the same solvent. For example, two color coats (2 coats) or two color coats and one top coat (3 coats) of products being evaluated can be applied to a nail spoon and allowed to dry for a designated period of time (for example, 5 days). Then, the number of strokes it takes to completely remove the composition from the nail spoons using a removal solvent and cotton pad can be counted.

"Substituted," as used herein, means comprising at least one substituent. Non-limiting examples of substituents for substitution include atoms, such as oxygen atoms and nitrogen atoms, as well as functional groups, such as hydroxyl groups, ether groups, alkoxy groups, acyloxyalky groups, oxyalkylene groups, polyoxyalkylene groups, carboxylic acid groups, amine groups, acylamino groups, amide groups, halogen containing groups, ester groups, thiol groups, sulphonate groups, thiosulphate groups, siloxane groups, and polysiloxane groups. The substituent(s) may be further substituted.

"Nail" as used herein includes fingernails as well as toenails.

"Volatile", as used herein, means having a flash point of less than about 100° C.

"Non-volatile", as used herein, means having a flash point of greater than about 100° C.

"Free" of an ingredient, as used herein, means that less than 1% of the identified ingredient is present in the composition (by weight with respect to the total weight of the composition). "Devoid" of an ingredient, as used herein, means that less than 0.5% of the identified ingredient is present in the composition (by weight with respect to the total weight of the composition). So, for example, a nail composition of the present invention which is "free of" wax contains less than 1% wax, and a nail composition which is "devoid of" wax contains less than 0.5% wax. A nail composition of the present invention may contain 0% of any ingredient, including wax, if desired.

"Solvent sensitive," as used herein, can be determined according to the following procedure: apply a thin layer of film forming agent (for example, latex) to a nail spoon and allow it to dry at 40° C. for three days. Then, using a cotton pad, remove the film from the spoon using acetone and count the number of strokes it takes to remove the film from the spoon. If it takes less than 10 strokes, it is "solvent sensitive."

The compositions, sets and methods of the present invention can comprise, consist of, or consist essentially of the essential elements and limitations of the invention described herein, as well as any additional or optional ingredients, components, or limitations described herein or otherwise useful. For example, the film-forming component of the nail composition can "consist essentially of" or "consist of" high molecular weight latex(es) comprising at least one styrene group, low molecular weight latex(es) lacking styrene groups, and low molecular weight sulfopolyester compound(s).

The "film-forming component" of the nail composition of the present invention comprises at least one high molecular weight latex comprising at least one styrene group, at least one latex lacking styrene groups, and at least one low molecular weight sulfopolyester compound. It may optionally further contain one or more additional film-forming agents. Preferably, the film-forming component contains a majority (greater than 50% by weight) of high molecular weight latex comprising at least one styrene group, latex lacking styrene groups, and low molecular weight sulfopolyester compound, preferably greater than 60% by weight, preferably greater than 70% by weight, preferably greater than 80% by weight, preferably greater than 90% by weight, and may contain up to 100% by weight of these film-forming agents, all percentages being based on total weight of the three film-forming agents with respect to the total weight of the film-forming component. All ranges and subranges within the percentages set forth above are included herein such as, for example, 10%-100% by weight, 25%-90% by weight, 50%-85% by weight, etc.

The "film-forming component" of the nail composition of the present invention preferably comprises from 10% to 60% by weight with respect to the total weight of the composition, preferably 15% to 50% by weight with respect to the total weight of the composition, and preferably from 20% to 40% by weight with respect to the total weight of the composition, including all ranges and subranges therebetween.

For purposes of the nail compositions and components of the present invention which "consist essentially of" identified ingredients, the "basic and novel properties" of such compositions and components are adhesion and removal properties.

For purposes of the methods of the present invention directed to improving adhesion properties and/or improving removal properties of a nail composition which "consists essentially of" identified ingredients, the "basic and novel property" of such methods is the property associated with the identified purpose(s) of the method. So, for example, "removal properties" is the basic and novel property associated with methods of improving removal properties of a nail composition, etc.

As indicated above, the nail compositions of the present invention comprise "latex," which is a colloidal dispersion of polymer particles in an aqueous liquid phase. "Latex" is generally obtained by suspension or emulsion polymerization or copolymerization of monomers according to processes that are well known to those of ordinary skill in the art. Such monomers may be chosen in particular from styrene, butadiene, acrylonitrile, chloroprene, vinyl acetate, urethanes, isoprene, isobutylene, and acrylic or methacrylic acid, maleic acid, crotonic acid or itaconic acid or esters or amides thereof.

High Molecular Weight Latex Comprising at Least One Styrene Group

In accordance with the present invention, nail compositions comprising at least one high molecular weight latex comprising at least one styrene group are provided.

As used herein, "high molecular weight" means more than 100,000 Da weight average molecular weight, preferably more than 120,000 Da, preferably more than 135,000 Da, and preferably more than 150,000 Da, including all ranges and subranges therebetween.

Any styrene acrylate copolymer or derivative thereof having the required molecular weight may be suitable for use in the compositions of the present invention. The high molecular weight latex comprising at least one styrene group preferably has a glass transition temperature (Tg) ranging from about −15° C. to about 90° C., such as from about 0° C. to about 50° C., including all ranges and subranges therebetween. For example, a copolymer comprising (1) styrene and ammonium acrylates, (2) acrylates, and/or (3) acrylic groups are suitable. A particularly preferred copolymer is a styrene/acrylates/ammonium methacrylate copolymer or a styrene acrylic copolymer, commercial examples of which include SYNTRAN 5620 and SYNTRAN 5760 (with or without paraben), by Interpolymer Corporation; JONCRYL 77, by BASF Performance Chemicals; and RHOPLEX P376, by Dow Chemical Company.

Preferably, the high molecular weight latex comprising at least one styrene group is present in the nail compositions of the present invention in an amount of active material ranging from about 1% to about 40%, more preferably from about 3% to about 35%, and preferably from about 5% to about 30%, by weight, based on the total weight of the composition, including all ranges and subranges in between.

Latex Lacking Styrene Groups

In accordance with the present invention, nail compositions comprising at least one latex lacking styrene groups are provided.

According to preferred embodiments, the latex lacking styrene groups are copolymers comprising two or more monomers chosen from acrylic acid, methacrylic acid, and their simple esters, for example, lower alkyl esters such as methyl, ethyl, and ethylhexyl esters. For example, copolymers may be chosen from acrylates copolymers, ammonium acrylates copolymers, ethyl acrylates copolymers, acrylates/ethylhexylacrylate copolymers, acrylates/octylacrylates copolymers, alkyl (meth)acrylates copolymers, acrylates/$C_{12}$-$C_{22}$ alkylmethacrylate copolymers, ethylacrylate/methacrylic acid copolymer, ethylhexyl acrylate/butyl acrylate/methacrylic acid, methyl methacrylate/butyl acrylate/methacrylic acid and t-butyl acrylate/ethyl acrylate/methacrylic acid copolymer. Examples of commercially available acrylate copolymers include, but are not limited to, DAITOSOL 3000 SLPN, DAITOSOL 4000 SJT, DAITOSOL 5000 AD, DAITOSOL 5000 SJ, KOBOGUARD® 50A, and KOBOGUARD® 50N sold by Kobo Products, Inc.

According to preferred embodiments, the latex lacking styrene groups comprises at least one monomer which is acrylic acid or methacrylic acid.

According to preferred embodiments, the latex lacking styrene groups is solvent sensitive.

Preferably, the latex lacking styrene groups is present in the nail compositions of the present invention in an amount of active material ranging from about 2% to about 40%, more preferably from about 5% to about 30%, and preferably from about 7.5% to about 25%, by weight, based on the total weight of the composition, including all ranges and subranges in between.

Low Molecular Weight Sulfopolyester Compound

In accordance with the present invention, nail compositions comprising at least one low molecular weight sulfopolyester compound are provided.

As used herein, "sulfopolyester compound" means a polymeric compound made from glycol(s), aromatic diacid(s), phthalic acid(s) and neutralized phthalic acid sulfonates. The sulfopolyester compound may be made from additional monomers in addition to the four identified monomers—that is, the sulfopolyester compound may "comprise" the four identified monomers, or it may "consist essentially of" the four identified monomers. The sulfopolyester compound may also "consist of" only the four identified monomers.

Suitable glycols include, but are not limited to, alkylene glycols and diglycols such as ethylene glycol, propylene glycol, ethylene diglycol and propylene diglycol.

Suitable aromatic diacids include, but are not limited to, cyclohexanedialkanols such as, for example, cyclohexanedimethanol, cyclohexanediethanol, cycloexanedipropanol, cyclohexanedibutanol, cyclohexandiisobutanol, etc., and cyclopentanedialkanols such as, for example, cyclopentanedimethanol, cyclopentanediethanol, etc.

Suitable phthalic acids include, but are not limited to, isophthalic acid and terphthalic acid.

Suitable neutralized phthalic acid sulfonates include, but are not limited to, alkali isophthalic acid sulfonates such as sodium isophthalic acid sulfonates, potassium isophthalic acid sulfonates, etc., and alkali terphthalic acid sulfonates such as sodium terphthalic acid sulfonate and potassium terphthalic acid sulfonate.

As used herein, "low molecular weight" means less than 75,000 Da weight average molecular weight, preferably less than 60,000 Da, preferably less than 50,000 Da, and preferably less than 40,000 Da, including all ranges and subranges therebetween.

According to preferred embodiments, the low molecular weight sulfopolyester compound is polyester-1 or polyester-5, a diethylene glycol/phthalate/isophthalate/1,4-cyclohexanedimethanol copolymer (INCI name: diglycol/CHDM/isophthalates/SIP copolymer) sold under the names Eastman AQ polymer (AQ35S, AQ38S, AQ55S, AQ48 Ultra) by the company Eastman Chemical.

Preferably, the low molecular weight sulfopolyester compound is present in the nail compositions of the present invention in an amount of active material sufficient to improve adhesion and/or removal properties of the composition. Preferably, the low molecular weight sulfopolyester compound is present in the nail compositions of the present invention in an amount of active material ranging from about 0.5% to about 20%, more preferably from about 0.75% to about 7.5%, and preferably from about 1% to about 5%, by weight, based on the total weight of the composition, including all ranges and subranges in between.

Preferably, the low molecular weight sulfopolyester compound and the latex lacking styrene groups active materials are present in a weight ratio of from about 1:1 to about 1:50, preferably from about 1:1.5 to about 1:30, and preferably about 1:2 to about 1:25, including all ranges and subranges therebetween.

Preferably, the low molecular weight sulfopolyester compound and the high molecular weight latex comprising at least one styrene group active materials are present in a weight ratio of from about 2:1 to about 1:60, preferably from about 1.5:1 to about 1:40, and preferably about 1:1 to about 1:30, including all ranges and subranges therebetween.

Preferably, the latex lacking styrene groups and the high molecular weight latex comprising at least one styrene group active materials are present in a weight ratio of from about 6:1 to about 1:6 preferably from about 5:1 to about 1:5, and most preferably about 4:1 to about 1:4, including all ranges and subranges therebetween.

Water

According to preferred embodiments, the nail compositions of the present invention comprise water. Preferably, total water content in the nail compositions of the present invention ranges from about 20% to about 90%, more preferably from about 30% to about 80%, and more preferably from about 35% to about 70%, by weight, based on the total weight of the composition, including all ranges and subranges in between. According to preferred embodiments, the nail composition is "water-based," meaning that the continuous phase is aqueous.

Optional Ingredients

According to particularly preferred embodiments of the present invention, the nail compositions of the present invention optionally further comprise one or more ingredients selected from the group consisting of water-soluble film forming agents, coalescent agents, plasticizers, and coloring agents (colorants).

According to particularly preferred embodiments of the present application, nail compositions (film-forming component of the nail composition) further comprising at least one water-soluble film forming agent are provided. A "water-soluble film forming agent" is a polymer which can be dissolved in an aqueous phase.

Specific examples of suitable water-soluble film forming agents include, but are not limited to, proteins, such as proteins of plant origin, such as, for example, wheat or soya proteins; or proteins of animal origin, such as keratins, for example keratin hydrolysates and sulfonic keratins; cellulose polymers, such as, for example, hydroxyethylcellulose, hydroxypropylcellulose, methylcellulose or ethylhydroxyethylcellulose; acrylic polymers or copolymers, such as, for example, polyacrylates or polymethacrylates; vinyl polymers, such as, for example, polyvinylpyrrolidones, copolymers of methyl vinyl ether and of maleic anhydride, the copolymer of vinyl acetate and of crotonic acid, copolymers of vinylpyrrolidone and of vinyl acetate, copolymers of vinylpyrrolidone and of caprolactam, or polyvinyl alcohol; gums arabic, guar gum, xanthan derivatives or karaya gum; alginates and carrageenans; glycoaminoglycans, hyaluronic acid and its derivatives; shellac resin, gum sandarac, dammars, elemis or copals; muccopolysaccharides, such as chondroitin sulfates; and their mixtures.

According to preferred embodiments, the at least one water-soluble film forming agent, if present, is present in the compositions of the present invention in an amount of active material ranging from about 0.01 to about 30% by weight, more preferably from about 0.1 to about 20% by weight, and most preferably from about 1 to about 10% by weight, based on the total weight of the composition, including all ranges and subranges within these ranges.

According to particularly preferred embodiments of the present application, nail compositions further comprising at least one plasticizer and/or coalescent are provided. Plasticizers are additives used to optimize the mechanical properties of the films. They tend to reduce the Glass Transition Temperature (Tg) and increase the softness and flexibility of the films. Coalescents are additives used to aid the coalescence of the latex particles, and hence assisting the film formation process.

Preferably, the plasticizer has a distribution coefficient D of less than or equal to 0.1. The distribution coefficient can be determined in accordance with the teaching of "A method to predict the distribution coefficient of coalescing agents between latex particles and the water phase," *Progress in Organic Coatings*, vol. 30, 1997, pp. 173-177, the disclosure of which is specifically incorporated by reference herein.

Preferably, the plasticizer has a boiling point measured at ambient pressure of less than or equal to 285° C., preferably less than or equal to 270° C., and preferably less than or equal to 250° C. In the present specification, the boiling point values are to be considered accurate to ±2° C. owing to the uncertainties of boiling point measurement.

Any plasticizing agent typically found in nail compositions can be used. Examples of suitable plasticizers include, but are not limited to, glycols and their ester derivatives, esters of acids, in particular carboxylic acids, such as citrates, adipates, carbonates, tartrates, phosphates or sebacates, oxyethylenated derivatives, such as oxyethylenated oils, and their mixtures. For example, suitable plasticizing agents include, but are not limited to, diisobutyl adipate, the ester of teributyl acid and 2,2,4-trimethylpentane-1,3-diol, diethyl adipate, diethyl phthalate, dibutyl phthalate, dioctyl phthalate, butyl 2-ethylhexyl phthalate, dimethyl sebacate, dibutyl sebacate, ethyl stearate, 2-ethylhexyl palmitate, dipropylene glycol n-butyl ether, tributyl phosphate, tributoxyethyl phosphate, tricresyl phosphate, triphenyl phosphate, glycerol triacetate, butyl stearate, butyl glycolate, benzyl benzoate, butyl acetyltricinoleate, glyceryl acetyltricinoleate, dibutyl phthalate, diisobutyl phthalate, dioctyl phthalate, dimethoxyethyl phthalate, diamyl phthalate, triethyl citrate, tributyl citrate, tributyl acetylcitrate, tri(2-ethylhexyl) acetylcitrate, dibutyl tartrate, camphor, and mixtures thereof.

In accordance with preferred embodiments, the plasticizer, if present, is preferably present in the primer composition in an amount of from 0.1% to 20% by weight, preferably from 0.25% to 15% by weight, preferably from 0.5 to 10% by weight, of the total weight of the composition, including all ranges and subranges therebetween.

According to particularly preferred embodiments of the present application, nail compositions further comprising at least one coalescent agent are provided. The coalescent agent promotes the coalescence of the polymer(s) in the composition.

Preferably, the coalescent agent has a distribution coefficient D' of greater than or equal to 0.5, measured in accordance with the above-referenced "A method to predict the distribution coefficient of coalescing agents between latex particles and the water phase," *Progress in Organic Coatings*, vol. 30, 1997, pp. 173-177.

Preferably, the coalescent agent has a boiling point measured at ambient pressure ranging from 90° C. to 180° C., preferably from 150° C. to 180° C.

Any coalescent agent typically found in nail polish compositions can be used. Examples of suitable plasticizers include, but are not limited to, propylene glycol n-butyl ether, dipropylene glycol dimethyl ether, propylene glycol methyl ether acetate, propylene glycol propyl ether, methyl lactate, ethyl lactate, isopropyl lactate, and mixtures thereof.

In accordance with preferred embodiments, the coalescent agent, if present, is preferably present in the primer composition in an amount of from 0.1% to 20% by weight, preferably from 0.5% to 15% by weight, preferably from 1 to 10% by weight, of the total weight of the composition, including all ranges and subranges therebetween.

According to particularly preferred embodiments of the present application, nail compositions further comprising at least one colorant are provided. Any colorant typically found in nail compositions can be used. Suitable colorants include, but are not limited to, lipophilic dyes, pigments and pearlescent agents, and their mixtures.

Suitable examples of fat-soluble dyes are, for example, Sudan red, DC Red 17, DC Green 6, β-carotene, soybean oil, Sudan brown, DC Yellow 11, DC Violet 2, DC Orange 5 and quinoline yellow.

Suitable pigments can be white or colored, inorganic and/or organic and coated or uncoated. Mention may be made, for example, of inorganic pigments such as titanium dioxide, optionally surface treated, zirconium or cerium oxides and iron or chromium oxides, manganese violet, ultramarine blue, chromium hydrate and ferric blue. Mention may also be made, among organic pigments, of carbon black, pigments of D & C type and lakes based on cochineal carmine or on barium, strontium, calcium or aluminum, such as D&C Red No. 10, 11, 12, and 13, D&C Red No. 7, D&C Red No. 5 and 6, and D&D Red No. 34, as well as lakes such as D&C Yellow Lake No. 5 and D&C Red Lake No. 2.

Suitable pearlescent pigments can be chosen from, for example, white pearlescent pigments, such as mica covered with titanium oxide or with bismuth oxychloride, colored pearlescent pigments, such as titanium oxide-coated mica with iron oxides, titanium oxide-coated mica with in particular ferric blue or chromium oxide, or titanium oxide-coated mica with an organic pigment of the abovementioned type, and pearlescent pigments based on bismuth oxychloride.

In accordance with preferred embodiments, the colorant is preferably present in the nail composition in an amount of from 0.01% to 20% by weight, preferably from 0.1% to 15% by weight, preferably from 0.5 to 10% by weight, of the total weight of the composition, including all ranges and subranges therebetween.

However, in accordance with certain preferred embodiments, the colorant is preferably present in the nail composition in an amount of 7.5% or less by weight, preferably 6% or less by weight, preferably 5% or less by weight, of the total weight of the composition, including all ranges and subranges therebetween.

Auxiliaries/Additives

The compositions of the present invention may additionally comprise an additive or auxiliary commonly used in nail compositions and known to a person skilled in the art as being capable of being incorporated into a nail composition. Such additives or auxiliaries may be chosen from thickening agent, preservatives, fragrances, oils, waxes, surfactants, antioxidants, agents for combating free radicals, spreading agents, wetting agents, dispersing agents, antifoaming agents, neutralizing agents, stabilizing agents, active principles chosen from essential oils, UV screening agents, sunscreens, moisturizing agents, vitamins, proteins, ceramides, plant extracts, fibers, and the like, and their mixtures.

However, in accordance with certain preferred embodiments, the nail compositions of the present invention contain wax in an amount of 5% or less by weight, preferably 4% or less by weight, preferably 3% or less by weight, of the total weight of the composition, including all ranges and subranges therebetween. According to certain embodiments, the nail composition may be free of wax. According to certain embodiments, the nail composition may be devoid of wax. According the certain embodiments, the nail composition may not contain any wax. Embodiments containing minimal wax content as described in this paragraph further also contain minimal colorant content, with colorant preferably present in the nail composition in an amount of 5% or less by weight, preferably 4% or less by weight, preferably 3% or less by weight, of the total weight of the composition, including all ranges and subranges therebetween.

A person skilled in the art will take care to select the optional additional additives and/or the amount thereof such that the advantageous properties of the composition according to the invention are not substantially, adversely affected by the envisaged addition.

These substances may be selected variously by the person skilled in the art in order to prepare a composition which has the desired properties, for example, consistency or texture.

These additives may be present in the composition in a total amount of from 0% to 90% (such as from 0.01% to 80%) relative to the total weight of the composition and further such as from 0.1% to 50% (if present), including all ranges and subranges therebetween.

Needless to say, the composition of the invention should be cosmetically or dermatologically acceptable, i.e., it should contain a non-toxic physiologically acceptable. The composition may be in any galenic form normally employed in the cosmetic and dermatological fields which is suitable for topical administration onto nails.

Topcoat/Basecoat/Primer

According to preferred embodiments of the present invention, the kits and methods of the present invention may optionally further include at least one composition or coat selected from a topcoat composition, a basecoat composition, and a primer composition. The primer, basecoat and topcoat are optional in the nail composition kits and methods of the present invention. However, if present, any topcoat suitable for application to nails as a topcoat, any basecoat suitable for application to nails as a basecoat, and any primer suitable for application to nails as a primer can be used. That is, the topcoat, basecoat and primer employed in the present invention are not limited: as long as the topcoat, basecoat and primer are suitable for application to nails, they are suitable for the nail composition set of the present invention. Typically, topcoats provide shine and/or protection to color coats of nail composition sets, and basecoats or primers provide adhesion of the color coat to the nail. When a primer or basecoat composition is used in conjunction with a nail composition of the present invention, improved adhesion and/or removal properties associated with the present invention relate to improved adhesion and/or removal properties between the nail composition of the present invention and the basecoat or primer composition.

According to preferred embodiments of the present invention, methods of making up or protecting nails comprising applying to the nails at least one nail composition comprising water, at least one high molecular weight latex comprising at least one styrene group, at least one latex lacking styrene groups and at least one low molecular weight sulfopolyester compound to nails in an amount sufficient to makeup or protect the nails are provided. According to preferred embodiments, the nail composition is free of wax and/or contains less than 5% coloring agent.

According to preferred embodiments of the present invention, methods of making up or protecting nails comprising applying to the nails at least one nail composition comprising water, at least one high molecular weight latex comprising at least one styrene group, at least one latex lacking styrene groups, and at least one low molecular weight sulfopolyester compound, and at least one composition selected from a topcoat, a basecoat and a primer in an amount sufficient to makeup or protect the nails are provided. According to preferred embodiments, the nail composition is free of wax and/or contains less than 5% coloring agent.

"Making up" as used herein means to provide decoration (for example, color) to the nail. "Protecting" as used herein means to inhibit damage to the nail (for example, chipping) by providing a protective layer on the nail.

In accordance with preferred embodiments of the preceding methods, the nail compositions of the present invention are applied topically to the nails of a person in need of (desirous) the desired making up or protection of nails in an amount sufficient to achieve the desired result. The compositions may be applied to the desired area as needed.

According to preferred embodiments of the present invention, a kit comprising at least one nail composition comprising water, at least one high molecular weight latex comprising at least one styrene group, at least one latex lacking styrene groups, and at least one low molecular weight sulfopolyester compound is provided. Preferably, the kit further comprises one or more of the following compositions: a topcoat composition; a basecoat composition; and/or a primer composition. Preferably, the kit further comprises instructions for applying and/or removing a nail composition of the present invention. According to preferred embodiments, the nail composition is free of wax and/or contains less than 5% coloring agent.

According to preferred embodiments, methods for improving adhesion properties and/or removal properties of a nail composition comprising water, at least one high molecular weight latex comprising at least one styrene group and at least one latex lacking styrene groups comprising adding at least one low molecular weight sulfopolyester compound during preparation of the nail composition in an amount sufficient to improve adhesion and/or removal properties of the nail composition. Preferably, the nail composition is free of wax and/or contains less than 5% coloring agent.

The compositions according to the invention can be manufactured by known processes used generally in the cosmetics or dermatological field.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective measurements. The following examples are intended to illustrate the invention without limiting the scope as a result. The percentages are given on a weight basis.

EXAMPLES

Example 1

Testing Protocols

Gloss: Gloss was determined using a gloss meter. For this determination, a layer of the composition to be tested was spread on a contrast card using an automatic spreader. The layer covered at least the white background of the card. Then, gloss was measured at 20° on the white background using a Byk Gardner gloss meter of reference microTRI-GLOSS. This measurement was repeated 3 times, and the average gloss (in gloss units (GU)) is the average of the 3 measurements carried out.

Adhesion: Adhesive properties were also assessed. For this determination, 4 in.×3 in. squares of Vitronails® from IMS Inc. were buffed with OPI 280 grid buffer in one direction. Either the individual latexes, comparative or inventive compositions were applied individually to the Vitronails® substrate using a 3 MIL draw down bar. The samples were aged at RT for 24 hours. The adhesion was assessed by determining how difficult it is to remove the each individual layer from the Vitronails® substrate using the cross-hatch tape test (ASTM D3359). The adhesive properties were assessed from 1 to 5, where 5 meant good adhesion and 1 meant poor adhesion.

Removability: The removability was determined by applying either two color coats or one base coat, or two color coats and one top coat to a plastic nail spoon. Each individual coat was allowed to dry for at least five minutes before applying the next layer. The samples were aged at 40° C. for 3 days. A cotton pad containing either 100% acetone or commercially available non-acetone remover (ethyl acetate-based) (0.5 mL) was rubbed onto the surface of the nail spoon and the number of strokes needed to completely remove the nail enamel was tallied. If the number of strokes was less than 10, the formula would achieve a "5" for removability. If the number of strokes was between 10-20, it would achieve a "4." 20-30 would be "3" and 30-40 would be a "2" and 40+ strokes would be a "1."

Example 2

Nail Compositions 1-5

The following nail compositions, containing an increasing amounts of latex lacking styrene groups (acrylate copolymer) as compared to high molecular weight styrene acrylate latex (both in active amounts), were prepared:

|  | Composition 1 | Composition 2 | Composition 3 | Composition 4 | Composition 5 |
| --- | --- | --- | --- | --- | --- |
| Styrene Acrylate Copolymer | 38.75 | 29.1 | 19.4 | 9.9 | 0 |
| Acrylate Copolymer | 0 | 7.28 | 14.6 | 22.2 | 29.6 |
| Propoylene Glycol Butyl Ether | 2 | 1 | 1 | 0.4 | 0.4 |
| Tributyl Citrate | 3 | 2 | 2 | 0.8 | 0.8 |
| Caprylyl Glycol | 0.29 | 0.22 | 0.15 | 0.09 | 0 |
| Phenoxyethanol | 0.67 | 0.75 | 0.82 | 0.91 | 0.99 |
| water | 55.3 | 59.6 | 62 | 65.7 | 68.2 |

The adhesion, shine and removability properties of these compositions were assessed, and the results are reported in the Table below.

|  | Adhesion | Shine | Removability |
|---|---|---|---|
| Composition 1 | 5 | 61.1 | 1 |
| Composition 2 | 4 | 75.5 | 1 |
| Composition 3 | 4 | 73.7 | 2 |
| Composition 4 | 2.5 | 66.1 | 4 |
| Composition 5 | 1 | 62.2 | 5 |

Example 3

The following nail compositions were prepared. The compositions contained latex lacking styrene groups (acrylate copolymer) and high molecular weight styrene acrylate latex (both in active amounts) in amounts adjusted for increased amounts of sulfopolyester. The compositions contained similar total amounts of these three ingredients:

|  | Composition 6 | Composition 7 | Composition 8 |
|---|---|---|---|
| Styrene Acrylate Copolymer | 10 | 8.9 | 7.9 |
| Acrylate Copolymer | 21.7 | 19.6 | 17.3 |
| Sulfopolyester | 0 | 4 | 8 |
| Propylene Glycol Butyl Ether | 1 | 1 | 1 |
| Tributyl Citrate | 2 | 2 | 2 |
| Caprylyl Glycol | 0.07 | 0.07 | 0.06 |
| Phenoxyethanol | 0.9 | 0.8 | 0.71 |
| Water | 64.3 | 63.6 | 63.0 |

The adhesion, shine and removability properties of these compositions were assessed, and the results are reported in the Table below.

|  | Adhesion | Shine | Removability |
|---|---|---|---|
| Composition 6 | 4 | 65.1 | 4 |
| Composition 7 | 5 | 73.7 | 4 |
| Composition 8 | 5 | 75.3 | 5 |

Example 4

Multi-Layered Examples

The following basecoat and topcoat compositions were prepared:

|  | Inventive Top Coat Composition 1 | Inventive Top Coat Composition 2 |
|---|---|---|
| Styrene Acrylate Copolymer | 18.8 | 17.7 |
| Acrylate Copolymer | 12.1 | 13.0 |
| Sulfopolyester | X | 1.84 |
| Propylene Glycol Butyl Ether | 3 | 1 |
| Tributyl Citrate | 0 | 1 |
| Phenoxyethanol | 0.73 | 0.73 |
| Caprylyl Glycol | 0.74 | 0.74 |
| Laponite XLG | 0.33 | 0.3 |
| Sodium Tetrapyrophosphate | 0.03 | 0.03 |
| Water | 64.26 | 63.7 |

|  | Inventive Color Coat Composition 1 | Inventive Color Coat Composition 2 |
|---|---|---|
| Styrene Acrylate Copolymer | 16.5 | 8.28 |
| Acrylate Copolymer | 10.7 | 17.1 |
| Sulfopolyester | X | 1.63 |
| Propylene Glycol Butyl Ether | 2.64 | 0.85 |
| Tributyl Citrate |  | 0.9 |
| Caprylyl Glycol | 0.65 | 0.7 |
| Phenoxyethanol | 0.72 | 0.78 |
| Red 7 Pigment Paste | 8.8 | 7.2 |
| Laponite XLG | 0.4 | 0.45 |
| Sodium Tetrapyrophosphate | 0.04 | 0.045 |
| Water | 59.6 | 62.1 |

The removability properties of these compositions using different removal agents were assessed as compared to commercially-available water-based nail enamel compositions, and the results are reported in the tables below.

|  | No. Strokes needed to remove nail enamel | | |
|---|---|---|---|
| Two Coat Compositions (Two Color Coats Applied) | Acetone Remover | Ethyl Acetate Remover | Alcohol Remover |
| Market Benchmark 1 | 30 | 39 | 43 |
| Market Benchmark 2 | 50 | 31 | 41 |
| Inventive Color Coat Composition 2 | 9 | 7 | 12 |

|  | No. Strokes needed to remove nail enamel | | |
|---|---|---|---|
| Three Coat Compositions (Two Color Coats and One Top Coat Applied) | Acetone Remover | Ethyl Acetate Remover | Alcohol Remover |
| Market Benchmark 1 | 48 | 50 | 50 |
| Market Benchmark 2 | 50+ | 46 | 50+ |
| Inventive Color Coat Composition 2 + Inventive Top Coat Composition 2 | 20 | 21 | 29 |

What is claimed is:

1. A nail composition comprising water, at least one plasticizer, at least one high molecular weight latex comprising at least one styrene group, at least one latex lacking styrene groups, and at least one low molecular weight sulfopolyester compound, wherein the sulfopolyester compound is polyester-5, and wherein the composition is physiologically acceptable.

2. The nail composition of claim 1, further comprising at least one water-soluble film forming agent.

3. The nail composition of claim 1, wherein the composition is water-based.

4. The nail composition of claim 1, wherein the composition is free of wax.

5. The nail composition of claim 1, further comprising at least one colorant.

6. The nail composition of claim 5, wherein the colorant is present in the composition in an amount of less than 5% by weight based on the total weight of the composition.

7. The nail composition of claim 1, wherein the sulfopolyester compound is present in an amount ranging from about 0.5% to about 10% by weight based on the total weight of the composition.

8. The nail composition of claim 1, wherein the low molecular weight sulfopolyester compound and the latex lacking styrene groups active materials are present in a weight ratio of from about 1:3 to about 1:20.

9. The nail composition of claim 1, wherein the low molecular weight sulfopolyester compound and the high molecular weight latex comprising at least one styrene group active materials are present in a weight ratio of from about 1:3 to about 1:20.

10. The nail composition of claim 1, wherein the latex lacking styrene groups and the high molecular weight latex comprising at least one styrene group active materials are present in a weight ratio of from about 3:1 to about 1:3.

11. The nail composition of claim 1, wherein the high molecular weight latex comprising at least one styrene group is a styrene/acrylates latex having a weight average molecular weight of greater than 150,000 Da.

12. The nail composition of claim 1, wherein the latex lacking styrene groups has a weight average molecular weight of less than 40,000 Da.

13. The nail composition of claim 1, further comprising at least one thickening agent.

14. A nail composition set comprising the nail composition of claim 1.

15. A kit comprising (a) a nail composition of claim 1, and (b) one or more compositions selected from the group consisting of a topcoat composition, a basecoat composition, and a primer composition.

16. A method for improving adhesion properties and/or removal properties of a physiologically acceptable nail composition comprising water, at least one high molecular weight latex comprising at least one styrene group and at least one latex lacking styrene groups comprising adding at least one low molecular weight sulfopolyester compound, wherein the sulfopolyester compound is polyester-5, during preparation of the nail composition in an amount sufficient to improve adhesion and/or removal properties of the nail composition.

17. The method of claim 16, wherein the composition is free of wax.

18. The method of claim 16, wherein the composition contains less than 5% colorant.

19. The nail composition of claim 1, wherein composition does not contain a sunscreen agent.

20. A nail composition comprising water, at least one high molecular weight latex comprising at least one styrene group, at least one latex lacking styrene groups, and at least one low molecular weight sulfopolyester compound, wherein the sulfopolyester compound is polyester-5, wherein the composition is physiologically acceptable, and wherein the low molecular weight sulfopolyester compound and the latex lacking styrene groups active materials are present in a weight ratio of from about 1:3 to about 1:20.

21. A nail composition comprising water, at least one high molecular weight latex comprising at least one styrene group, at least one latex lacking styrene groups, and at least one low molecular weight sulfopolyester compound, wherein the sulfopolyester compound is polyester-5, wherein the composition is physiologically acceptable, and wherein the low molecular weight sulfopolyester compound and the high molecular weight latex comprising at least one styrene group active materials are present in a weight ratio of from about 1:3 to about 1:20.

22. A nail composition comprising water, at least one high molecular weight latex comprising at least one styrene group, at least one latex lacking styrene groups, and at least one low molecular weight sulfopolyester compound, wherein the sulfopolyester compound is polyester-5, wherein the composition is physiologically acceptable, and wherein the high molecular weight latex comprising at least one styrene group is a styrene/acrylates latex having a weight average molecular weight of greater than 150,000 Da.

23. A nail composition comprising water, at least one high molecular weight latex comprising at least one styrene group, at least one latex lacking styrene groups, and at least one low molecular weight sulfopolyester compound, wherein the sulfopolyester compound is polyester-5, wherein the composition is physiologically acceptable, and wherein the latex lacking styrene groups has a weight average molecular weight of less than 40,000 Da.

* * * * *